United States Patent [19]

Clark

[11] 4,402,862

[45] Sep. 6, 1983

[54] STABILIZATION OF HYGROSCOPIC SALTS

[75] Inventor: James H. Clark, Heslington, England

[73] Assignee: National Research Development Corporation, London, England

[21] Appl. No.: 380,448

[22] Filed: May 20, 1982

Related U.S. Application Data

[63] Continuation of Ser. No. 190,854, filed as PCT/GB79/00122, Jul. 19, 1979 published as WO80/00313. Mar. 7, 1980, abandoned.

[51] Int. Cl.$^3$ .................. B01J 31/24; B01J 31/18; B01J 27/12; C07C 45/45
[52] U.S. Cl. .................. 252/426; 252/428; 252/429 R; 252/430; 252/437; 252/438; 252/440; 252/441; 252/442; 252/194; 423/267; 423/268; 560/51; 568/21; 568/42; 568/309; 568/312; 568/937
[58] Field of Search .......... 252/194, 426, 428, 429 R, 252/430, 440, 442; 55/388; 423/267, 268, 499

[56] References Cited

U.S. PATENT DOCUMENTS

| | | | |
|---|---|---|---|
| 1,985,204 | 12/1934 | Derr et al. | 252/441 |
| 2,498,552 | 2/1950 | Kilgren et al. | 252/441 |
| 2,913,421 | 11/1959 | Horne et al. | 252/441 |
| 2,968,676 | 1/1961 | Potter, Jr. et al. | 252/442 |
| 3,555,102 | 1/1971 | Ogura et al. | 252/441 |
| 3,720,723 | 3/1973 | Pritchett | 252/441 |
| 3,728,405 | 4/1973 | Thoroughgood | 252/441 |
| 3,793,227 | 2/1974 | Snead et al. | 252/441 |
| 3,867,469 | 2/1975 | Ricks | 252/441 |
| 3,975,299 | 8/1976 | Crathorne | 252/432 |
| 3,983,175 | 9/1976 | Tamai et al. | 568/348 |
| 3,984,475 | 10/1976 | Tamai et al. | 568/316 |
| 4,033,764 | 7/1977 | Colegate | 252/455 Z |
| 4,157,312 | 6/1979 | Frame | 252/428 |

FOREIGN PATENT DOCUMENTS

| | | |
|---|---|---|
| 1097961 | 1/1961 | Fed. Rep. of Germany . |
| 2233097 | 1/1975 | France . |
| 2368454 | 5/1978 | France . |

OTHER PUBLICATIONS

Moffat; Catalysis Reviews–Sci. Eng., 18(2)–(1978), pp. 199–258.
Take et al.; Bull. Chem. Soc. Japan, 51(6), (1978), pp. 1581–1584.
Regen et al.; J.A.C.S.–99–(1977)–p. 3837.
Tundo; J.C.S. Chem. Comm., (1977)–pp. 641–642.
Keiman et al.; J. Org. Chem., 43(5), (1978), pp. 1020–1022.
Helmy et al.; Z. Phys. Chemie, Leipzig, 260(1979) 1, S.65–71.
The Condensed Chemical Dictionary–8th Edition Gessner G. Hawley–Van Nostrand Reinhold Co., p. 187.

Primary Examiner—P. E. Konopka
Attorney, Agent, or Firm—Oblon, Fisher, Spivak, McClelland & Maier

[57] ABSTRACT

The invention relates to the stabilization against water uptake of hygroscopic salts useful as catalysts by formation of anhydrous adducts with particulate support materials in order to facilitate manipulation and storage. The adducts comprise a particulate support material and a hygroscopic salt of a species of formula $R^1R^2R^3R^4N$, $R^1R^2R^3R^4P$, $R^1R^2R^3R^4As$, wherein $R^1R^4$ which may be identical or different represent hydrogen or alkyl or aryl groups, or of Li, Na, K, Rb, Cs, Be, Mg, Ca, Sr, Ba, Cu. Ag, Zn, Cd, Au, Hg, Ga, In, Tl, Sn, Sb or Pb, the salt anion being fluoride, bromide, chloride, sulphate, nitrate, nitrite, cyanate, thiocyanate, peroxide, hydroxide, acetate, formate or comprises phosphorus and oxygen, the salt being coated on the support material thereby being rendered less hygroscopic; provided that when the species is Na, the anion is other than hydroxide and when the species is Tl the anion is fluoride, bromide or chloride. Adducts of salts useful in catalytic fluorination, e.g. $R^1R^2R^3R^4N^+F^-$ and CsF are of especial interest.

10 Claims, No Drawings

STABILIZATION OF HYGROSCOPIC SALTS

This is a continuation of application Ser. No. 190,854, filed Mar. 7, 1980, now abandoned.

This invention relates to the stabilisation of hygroscopic salts.

Many salts such as fluorides which find application as catalysts for example are highly hygroscopic. It is therefore necessary to maintain and store them under anhydrous conditions and in particular to protect them from atmospheric hydration so that activity is not impaired.

It has now been found that such salts can be readily stabilised so that the rate of uptake of moisture from the atmosphere is significantly reduced, facilitating manipulation and storage.

Accordingly, the present invention comprises an anhydrous adduct of a particulate support material with a hygroscopic salt of a species of formula $R^1R^2R^3R^4N$, $R^1R^2R^3R^4P$, $R^1R^2R^3R^4As$, wherein $R^1-R^4$ which may be identical or different represent hydrogen or alkyl or aryl groups, or of Li, Na, K, Rb, Cs, Be, Mg, Ca, Sr, Ba, Cu, Ag, Zn, Cd, Au, Hg, Ga, In, Tl, Sn, Sb or Pb, the salt anion being fluoride, bromide, chloride, sulphate, nitrate, nitrite, cyanate, thiocyanate, peroxide, hydroxide, acetate, formate or comprises phosphorus and oxygen, the salt being coated on the support material thereby being rendered less hygroscopic; provided that when the species is Na, the anion is other than hydroxide and when the species is Tl the anion is fluoride, bromide or chloride.

Suitable support materials are generally solids which have surface groups capable of forming hydrogen bonds with the anion of the salt. Materials which have surface hydroxyl, amino or amido groups are of particular interest and especially silica gel, the zeolites, e.g. molecular sieves, alumina, diatomaceous earths such as celite and kaolin, porous glasses, proteins and cellulose. The support material may be hygroscopic, taking up a measurable amount of water from the atmosphere and is preferably at least as hygroscopic as cellulose, for many applications being significantly more so.

The present invention is particularly applicable of stabilising salts the hygroscopic nature of which is attributable to the anions present therein. Salts in which the anion is a halide are of particular interest and fluorides especially so. Anions which comprise phosphorus and oxygen include for example $-HPO_2$. Salts of $R^1R^2R^3R^4N$, including $NH_4$, $R^1R^2R^3R^4P$, $R^1R^2R^3R^4As$, Na, K, Rb, Cs, Mg, Ca, Cu, Ag, Zn, and Tl are of particular interest. Alkyl and aryl groups of formula $R^1-R^4$ may be unsubstituted or substituted, e.g. by hydroxyl groups, and alkyl groups may be lower alkyl, e.g. $C_1-C_6$ groups or higher alkyl groups. Salts of formula $R^1R^2R^3R^4N^+F^-$, CaF and $ZnCl_2$ of especial interest. It is envisaged that in the adduct the anions of the salt are stabilised in relation to water uptake by hydrogen bonding between said anions and surface groups, e.g. OH groups on the surface of the support material. The support material present in the adduct may in some cases comprise, in addition to groups bonded to the salt, other groups produced for example by exchange of surface groups originally present in the support material with salt anions during preparation of the adduct. A minority of surface hydroxyl groups in the support material may, for example, exchange with fluoride ions during preparation of fluoride adducts.

The pore size of the material is usually dependent on the salt which is to be rendered hygroscopic and in particular on the size of the cation. The mean pore size is generally at least 6 Å and preferably at least 20 Å. It is particularly preferred that the pore size be at least 20 Å when the cation is a tetra-alkyl ammonium or tetra-aryl ammonium salt especially when the support material is silica.

The present invention also includes within its scope a method of rendering a hygroscopic salt as hereinbefore defined less hygroscopic, which comprises treating the salt with a particulate support material so that an adduct is formed between the support material and the salt. The adduct may be conveniently formed by treating a solution of the salt in a solvent such as water with the insoluble support material and removing the solvent, for example by evaporation. This method is particularly convenient for the treatment of tetra-alkyl ammonium fluorides which may be prepared from aqueous solution of the readily available corresponding hydroxides. In general the quantities of support and salt are so chosen that there are present at least as many surface active groups on the support material capable of binding the salt as there are anions of the latter. In addition to rendering the salt less hygroscopic the method of the present invention enables highly anhydrous materials to be produced with great convenience.

Adducts of the present invention find wide application as sources of anions.

According to a further aspect of the present invention, in a chemical process there is provided as a source of an anion which participates in the process an adduct hereinbefore defined of a particulate support material with a hygroscopic salt, the salt being coated on the support and thereby being rendered less hygroscopic.

The adduct finds particular application as a source of anion such as fluoride for reactions conducted in anhydrous media.

Chemical reactions in which the adduct finds application may be catalytic or non-catalytic. Reactions of particular interest include those reactions which are normally conducted by disposing reactants and/or substrate with the anion source in the same phase (usually a liquid phase). Use of the present adduct allows many such reactions to proceed at comparable rates although the anion source is disposed as a separate solid phase from the reactants and substrates disposed in another, e.g. liquid phase. Reactions in which the adduct of the present invention may find application as a catalyst include fluorination, for example fluorine replacement of chlorine or bromine in the nucleus of an aromatic compound e.g. 2-chloronitrobenzene or 2,5-dichloronitrobenzene by treatment of the compound with a source of fluorine, such as KF, in the presence of an adduct comprising a fluoride such as CaF. In the latter case the substrate is generally disposed in a liquid phase and the catalyst is present as a separate solid phase.

Non-catalytic reactions of particular interest include esterification.

The invention is illustrated by the following Examples.

EXAMPLE 1

Preparation of Tetrabutylammonium fluoride-silica reagent (TBAF-silica reagent)

A round-bottomed flask is charged with 20 g of 20% aqueous TBAF and 10 g of 60-120 mesh silica gel (BDH chromatographic grade, purified by treatment with HCl and dried at 150°–200° C.; mean pore size 21 Å, surface area 850 m²/g is added. The slurry becomes warm on shaking. The flask is then transferred to a rotary evaporator and the water is removed, 100 ml of methanol is added and the evaporation continued. On removal of the solvents, the resulting solid is washed with ether and dried in vacuo, over $P_2O_5$. The yield of the product (14 g) (corresponding to 1 mmole TBAF (0.26 g)/g TBAF-silica) suggests that all of the water has been removed. The final material is stable, nonhygroscopic and remains an effective catalyst after being left in air for several days.

EXAMPLE 2

Preparation of benzyltrimethylammonium fluoride-silica (BTMAF-silica)

BTMAF-silica is prepared by the method of Example 1 in which TBAF is replaced by the corresponding molar amount of BTMAF.

EXAMPLE 3

Preparation of tetraethylammonium fluoride-silica

Tetraethylammonium fluoride-silica is prepared by a method identical to that described in Example 1 but in which TBAF is replaced by the corresponding molar quantity of tetraethylammonium fluoride.

Thermal stability

TBAF-silica does not lose any significant amount of fluoride after several hours at 120° C. At 150° C. there is a steady loss in fluoride with some 60–70% of the fluoride being lost after some 9 h. The benzyltrimethylammonium fluoride (BTMAF)-silica and tetraethylammonium fluoride (TEAF)-silica reagents are stable to 120° C. and the alkali metal fluoride-silica reagents would seem to be stable to much higher temperatures. The tetraalkylammonium fluoride-silica reagents may be burned (offering a quick method for detecting whether the salt is present) resulting in loss of fluoride and leaving a greyish residue. On burning, these materials give off fumes of a basic substance, the thermal decomposition probably produces amine, alkene and bifluoride (which itself will decompose).

Air stability

The materials prepared do not lose or gain weight (significantly) on standing in air over a period of several days.

Solvent stability

When the TBAF-silica and BTMAF-silica reagents are treated with various common solvents (generally ca. 50 cm³/g of reagent) for varying amounts of time, the conclusions are essentially the same for both materials. Complete removal of fluoride may be accomplished by stirring with water for 2–6 h. at room temperature (the alkali metal fluoride reagents lose their fluoride on washing with water) or by stirring with methanol for ca. 2 h. or less (room temperature). Partial loss of fluoride is achieved by stirring the materials at room temperature for several hours in various other protic solvents such as acetic acid, and ethanol. Chloroform may remove small amounts of fluoride and may be used to remove excess fluoride (more than 1–2 mmoles of fluoride/g. of reagent). All of the silica reagents studied are completely unaffected by stirring with tetrahydrofuran for several hours at room temperature. The reagents are similarly unaffected by dimethylformamide (DMF).

EXAMPLE 4

Preparation of 4-nitro-1,3-diphenylbutanone 1 g of IBAF-silica (ca. 1 mmole equiv. $\overline{F}$) is suspended in 20 ml of THF containing 6.1 g (0.1 mole) of nitromethane and 1.04 g (5 mmole) of chalcone and the resulting mixture heated with stirring. to 60° C. for 1 h. Separation (the cooled reaction mixture is filtered, the residue washed with ether and the combined filtrates evaporated to dryness) and recrystallisation of the product from ethanol gives 1.16 g (86%) of 4-nitro-1,3-diphenylbutanone, m.p. 99°–100° C. The TBAF-silica is recovered in 95% yield. The same experiment carried out at room temperature gives a 75% yield of recrystallised product and a 99% yield of recovered TBAF-silica after 6 h. On repeating the room-temperature experiment using recovered TBAF-silica, a 70% yield of recrystallised product and ca. 97% of TBAF-silica are recovered after 6 h. A control experiment carried out in which the TBAF-silica is replaced by silica along gives no detectable product (by $^1H$ n.m.r.) after 12 h. at room temperature.

EXAMPLE 5

MICHAEL ADDITION (1)

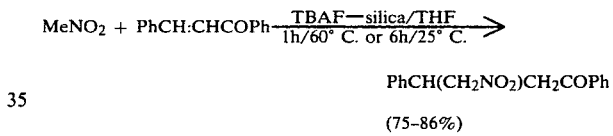

PhCH(CH₂NO₂)CH₂COPh (75–86%)

TEAF-silica and BTMAF-silica gives 75% product after 5–6 h. at 25° C.; silica alone gives no detectable product after 12 h. at 25° C., the recovered fluoride-silica reagents give ca. 70% yields of product after 5–7 h/25° C.; reagents formed by mutual dehydration (same conditions as with the silica reagents) of mixtures of TBAF or BTMAF with celite, alumina (neutral and acidic) and porous glass (1 g reagent contains 1 mmole of fluoride) gave 65–85% yields of products after 6–7 h/25° C. the residues in these reactions are shown to contain less fluoride than the starting materials and are significantly less effective in the same reaction.

The above compares to a yield of 94% for the same reaction using KF/18-crown-6 as the catalyst for a period of 1.5 h at 81° C. (J.C.S.Chem.Comm. 1977, 237).

EXAMPLE 6

MICHAEL ADDITION (2)

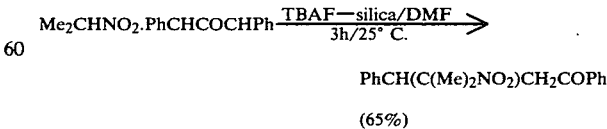

PhCH(C(Me)₂NO₂)CH₂COPh (65%)

Similarly with TEAF and BTMAF silica reagents.

The above compares to a ca. 84% yield for the same reaction using TEAF which had been previously converted to its 2-nitropropane solvate. for 4 h at 25° C.

EXAMPLE 7
THIOL ADDITION

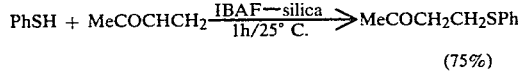

(75%)

Similarly with TEAF and BTMAF silica reagents.

The above compares to a 98% yield for the same reaction using TBAF which had been rigorously dried for some 20 h. before use for 1 h. at 20° C. (Synthesis, 1976, 602).

EXAMPLE 8
OXIDATION (1)

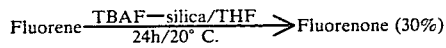

EXAMPLE 9
OXIDATION (2)

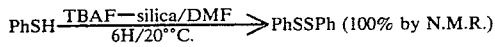

EXAMPLE 10
SULPHENYLATION

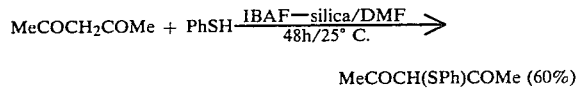

MeCOCH(SPh)COMe (60%)

The above compares to an 81% yield for the same reaction using the TBAF solvate of the diketone for 20 h. at 25° C. (Can. J. Chem. 1978 141).

In Examples 5–10 a 10 mole percent equivalent of fluoride (1 mmole fluoride/g of reagent) is employed which is recoverable. In the following examples illustrating non-catalytic reactions, a 200 mole percent equivalent of fluoride is used which is not recoverable although the silica gel can be recovered by washing the residue with chloroform to remove bromide or iodide.

EXAMPLE 11
PHENACYL ESTER SYNTHESIS

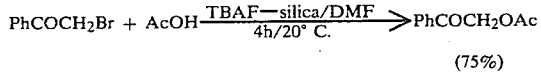

(75%)

EXAMPLE 12
C-ALKYLATION

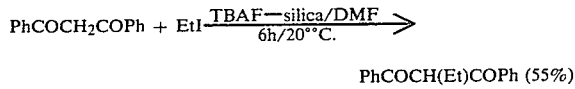

PhCOCH(Et)COPh (55%)

The above compares to a 92% yield for the same reaction using TBAF-diketone solvate for 2 h. at 20° C. (J.C.S. Perkin, 1977, 1743).

EXAMPLE 13
Preparation of caesium fluoride-silica (CsF-silica)

A round-bottomed flask is charged with 1.79 g of CsF in ca. 50 cm$^3$ of deionized water and 10 g of 60–120 mesh silica gel (BDH chromatographic grade, purified by treatment with HCl and dried at 150°–200° C.; mean pore size 21 Å, surface area 850 m$^2$/g) is added. The slurry is stirred at ambient temperature for ca. 30 minutes. The flask is transferred to a rotary evaporator and the water is removed under reduced pressure. On removal of the water, the resulting solid is dried at 150° C. to constant weight or for ca. 4 hours. The weight of the product (11.8 g) (corresponding to 1 mmole CsF (0.152 g)/g CsF-silica) suggests that all of the water has been removed. The final anhydrous material is a white, particulate solid which remains free-flowing after prolonged exposure to the atmosphere.

EXAMPLE 14
FLUORINATION
Preparation of 2-fluoronitrobenzene

A finely ground mixture of potassium fluoride (11.62 g, 0.2 mole) and CsF-silica (5 g, ca. 5 mmole equiv. $\overline{F}$) is dried at 150° C. and then immediately transferred to a three-necked flask containing 2-chloronitrobenzene (7.88 g, 0.05 mole) and dimethylformamide. The flask is connected to a water-condenser and a mechanical stirrer and the reaction mixture is brought to reflux with vigorous stirring. After 24 h. the reaction mixture is cooled and separated into its ether- and water-soluble components. Chloride analysis of the aqueous extracts (AgNO$_3$ titration, K$_2$CrO$_4$ indicator) shows better than 60% conversion of the 2-chloronitrobenzene. The ethereal extracts are washed with water (to remove the D.M.F.), dried over anhydrous Na$_2$SO$_4$, evaporated to dryness on a rotary evaporator and distilled under reduced pressure to give 3.7 g (52%) of 2-fluoronitrobenzene, b.p. 68°–70° C. (4 Torr). When the same reaction is carried out using (i) a dried mixture of KF (11.62 g) and CsF (0.75 g) and (ii) dried KF (11.62 g) alone in place of the KF-CsF-silica mix, chloride analysis of the aqueous extracts shows ca. 60% and ca. 20% conversion of 2-chloronitrobenzene respectively.

EXAMPLE 15

Replacing of dimethylformamide by 75 g tetramethylene sulphone in the reaction of Example 14 which uses KF-CsF-silica and carrying out the reaction at ca. 220° C. for 16 h. (reagent quantities being identical to those used before) gives ca. 100% conversion of 2-chloronitrobenzene to 2-fluoronitrobenzene (by chloride analysis).

EXAMPLE 16

10.1 g (0.05 mol) 2,5-dichloronitrobenzene, 11.62 g KF (anhydrous), 5 g (ca 5 mmole equiv. $\overline{F}$) CsF-silica (anhydrous) and 75 g tetramethylene sulphone react together at ca. 210° C. for 16 h. to produce ca. 0.05 mole equiv. of $\overline{Cl}$.

I claim:

1. An anhydrous adduct of a first substance, which is a particulate support material having a plurality of surface groups respectively capable of hydrogen bonding a salt anion, with a second substance, which consists essentially of a hygroscopic salt of a species of formula $R^1R^2R^3R^4N$, $R^1R^2R^3R^4P$, $R^1R^2R^3R^4As$, wherein $R^1$–$R^4$ which may be identical or different represent alkyl or aryl groups, the salt anion being fluoride, chloride, bromide, sulphate, nitrate, nitrite, cyanate, thiocyanate, peroxide, hydroxide, acetate, formate or comprises phosphorous and oxygen; the second substance being coated on the support material, thereby rendering said second substance less hygroscopic by said hydrogen bonding wherein the quantities of support and salt are chosen such that there are present at least as many surface active groups on the support material capable of hydrogen bonding as there are anions of said salt.

2. An adduct according to claim 1, in which the salt is of $R^1R^2R^3R^4N$.

3. An adduct according to claim 1, in which the salt anion is fluoride, chloride, bromide or hydroxide.

4. An adduct according to claim 3, in which the anion is fluoride.

5. An adduct according to claim 1, in which the salt is $R^1R^2R^3R^4N^+F^-$.

6. An adduct according to claim 1, in which the support material has surface hydroxyl, amino or amido groups.

7. An adduct according to claim 1, in which the support material comprises silica gel, a zeolite, alumina, a diatomaceous earth, a porous glass, a protein or cellulose.

8. An adduct according to claim 1, in which the mean pore size is at least 20 Å.

9. A method of rendering a substance consisting essentially of a hygroscopic salt less hygroscopic which comprises contacting the substance with a particulate support material so that an adduct is formed between the support material and the salt, wherein the hygroscopic salt consists essentially of a species of formula $R^1R^2R^3R^4N$, $R^1R^2R^3R^4P$, $R^1R^2R^3R^4As$ wherein $R^1$–$R^4$ which may be identical or different represent alkyl or aryl groups, the salt anion being fluoride, chloride, bromide, sulphate, nitrate, nitrite, cyanate, thiocyanate, peroxide, hydroxide, acetate, formate or comprises phosphorus and oxygen, and , wherein the quantities of support and salt are chosen such that there are present at least as many surface active groups on the support material capable of hydrogen bonding as there are anions of said salt.

10. The method according to claim 9, in which a solution of the salt in a solvent is contacted with insoluble support material and the solvent is subsequently removed.

* * * * *

UNITED STATES PATENT AND TRADEMARK OFFICE
CERTIFICATE OF CORRECTION

PATENT NO. : 4,402,862

DATED : September 6, 1983

INVENTOR(S) : Clark, James H.

It is certified that error appears in the above-identified patent and that said Letters Patent is hereby corrected as shown below:

On the title page insert
--[30] Foreign Application Priority Data

July 26, 1978  Great Britain.....31193/78

Signed and Sealed this

Twenty-eighth Day of August 1984

[SEAL]

Attest:

GERALD J. MOSSINGHOFF

Attesting Officer

Commissioner of Patents and Trademarks